(12) United States Patent
Bacik et al.

(10) Patent No.: US 8,815,174 B2
(45) Date of Patent: Aug. 26, 2014

(54) STEAM STERILIZER

(71) Applicant: American Sterilizer Company, Mentor, OH (US)

(72) Inventors: Michael A Bacik, Fairview, PA (US); Peter J Buczynski, Girard, PA (US); Francis J Zelina, Lake City, PA (US); Jeffrey C Robertson, Rochester, NY (US)

(73) Assignee: American Sterilizer Company, Mentor, OH (US)

( * ) Notice: Subject to any disclaimer, the term of this patent is extended or adjusted under 35 U.S.C. 154(b) by 56 days.

(21) Appl. No.: 13/798,806

(22) Filed: Mar. 13, 2013

(65) Prior Publication Data
US 2014/0050634 A1  Feb. 20, 2014

Related U.S. Application Data

(60) Provisional application No. 61/684,355, filed on Aug. 17, 2012.

(51) Int. Cl.
| | | |
|---|---|---|
| *A61L 2/00* | (2006.01) | |
| *A24F 27/00* | (2006.01) | |
| *B65D 1/40* | (2006.01) | |
| *A47J 39/00* | (2006.01) | |
| *B65D 25/00* | (2006.01) | |
| *A61L 2/07* | (2006.01) | |

(52) U.S. Cl.
CPC ........................................ *A61L 2/07* (2013.01)
USPC ........... 422/300; 422/294; 422/297; 422/305; 206/96; 206/134; 206/438; 220/62.11; 220/694; 220/592.28; 220/592.2

(58) Field of Classification Search
CPC ............. A61J 1/00; B65D 81/38; A61L 2/00; A61L 2/07; A61L 9/12
USPC ............ 422/26, 28, 547, 554, 560, 294, 297, 422/300, 305, 939; 206/96, 134, 438; 34/664, 665, 184; 220/62.11, 694, 220/592.28, 592.2, 739; 604/224
See application file for complete search history.

(56) References Cited

U.S. PATENT DOCUMENTS

| | | | |
|---|---|---|---|
| 5,288,467 A | 2/1994 | Biermaier | 422/116 |
| 5,314,668 A | 5/1994 | Biermaier | 422/292 |

(Continued)

OTHER PUBLICATIONS

Int'l Search Report from corresponding Int'l (PCT) App. No. PCT/US13/35582, 2 pages.

(Continued)

*Primary Examiner* — Monzer R Chorbaji
(74) *Attorney, Agent, or Firm* — Kusner & Jaffe; Michael A. Centanni

(57) ABSTRACT

A sterilizer having a cassette for holding metal instruments or medical devices. The cassette includes a metallic container that defines a sterilization chamber. The container has at least one outer surface. A plurality of spaced-apart, elongated rails extend along the at least one outer surface of the container. Each of the rails includes a free, longitudinal edge wherein the edges of the rails lie in a first plane. An insulating shell encases the metallic container and the plurality of rails. An outer surface of the insulating shell lies in the first plane. A receiving unit includes a housing having an outer surface and an inner surface. The inner surface engages the edges of the rails and the outer surface of the insulating shell when the cassette is disposed within the inner housing. A plurality of spaced-apart elongated ribs extends along the outer surface of the housing.

37 Claims, 7 Drawing Sheets

(56) References Cited

U.S. PATENT DOCUMENTS

| | | | |
|---|---|---|---|
| 5,424,047 A | 6/1995 | Zwingenberger et al. | 422/296 |
| 5,543,119 A | 8/1996 | Sutter et al. | 422/299 |
| 5,545,383 A | 8/1996 | Zwingenberger et al. | 422/295 |
| 5,551,462 A | 9/1996 | Biermaier | 134/166 |
| 5,795,403 A | 8/1998 | Biermaier | 134/22.12 |
| 5,993,754 A | 11/1999 | Lemmen et al. | 422/293 |
| 6,113,574 A | 9/2000 | Spinello | 604/131 |
| 6,585,943 B1 | 7/2003 | Sanford et al. | 422/307 |
| 7,276,023 B2 | 10/2007 | Annecke | 600/101 |
| 7,462,586 B2 | 12/2008 | Tijanic et al. | 510/161 |
| 7,476,369 B2 | 1/2009 | Yin et al. | 422/298 |
| 7,641,852 B1 | 1/2010 | McPhail et al. | 422/26 |
| D632,800 S | 2/2011 | Nanni et al. | D24/217 |
| 2005/0130473 A1 | 6/2005 | Annecke | 439/135 |
| 2005/0196315 A1* | 9/2005 | Babko-Malyi et al. | 422/23 |
| 2009/0093389 A1 | 4/2009 | Tijanic et al. | 510/161 |
| 2011/0262301 A1 | 10/2011 | Ghelman et al. | 422/26 |

OTHER PUBLICATIONS

SciCanUSA, STAT*IM* 7000, Product Information obtained from website www.scicanusa.com, last accessed Apr. 22, 2011.

* cited by examiner

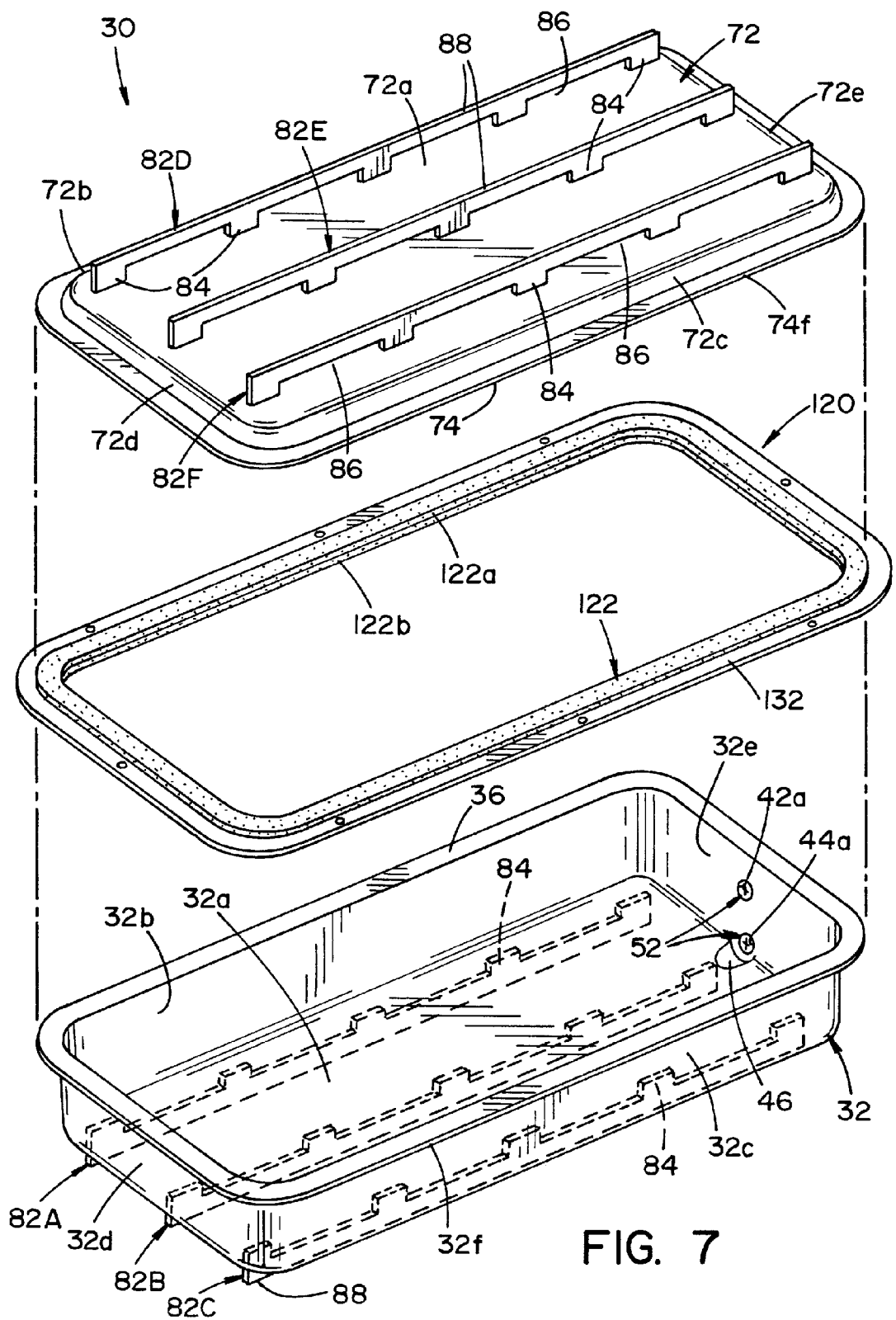

_US 8,815,174 B2_

STEAM STERILIZER

RELATED APPLICATIONS

This application claims the benefit of U.S. Provisional Application No. 61/684,355, filed Aug. 17, 2012, which is fully incorporated herein by reference.

FIELD OF THE INVENTION

The present invention relates generally to sterilizers and, more particularly, to a compact steam sterilizer for sterilizing medical instruments and medical devices.

BACKGROUND OF THE INVENTION

It is known to sterilize small sets of medical instruments or medical devices in metal trays or metal cassettes. One requirement for steam sterilizers that sterilize medical instruments and medical equipment is that the instrument or device to be sterilized be subject to saturated steam at a prescribed temperature for a prescribed period of time. As a result of the exposure to the steam, the metal trays and cassettes become extremely hot and difficult to handle following a sterilization process.

The present invention relates to a steam sterilizer for sterilizing medical instruments and medical devices within a cassette wherein a sterilization chamber within the cassette may be subjected to saturated steam at the prescribed temperature for the prescribed period of time and yet the cassette may be safely handled by a user shortly after the sterilization period has ended.

SUMMARY OF THE INVENTION

In accordance with a preferred embodiment of the present invention, there is provided a sterilizer comprised of a cassette for holding metal instruments or medical devices. The cassette comprises a metallic container that defines a sterilization chamber for holding the metal instruments or medical devices. The container has at least one outer surface. A plurality of spaced-apart, elongated rails extend along the at least one outer surface of the container. Each of the rails includes a free, longitudinal edge facing outwardly away from the at least one outer surface of the container wherein the edges of the rails lie in a first plane. An insulating shell encases the metallic container and the plurality of rails wherein an outer surface of the insulating shell lies in the first plane. A receiving unit receives the cassette. The receiving unit comprises a housing having an outer surface and an inner surface. The inner surface engages the edges of the rails and the outer surface of the insulating shell when the cassette is disposed within the housing. A plurality of spaced-apart, elongated ribs extends along the outer surface of the housing.

In accordance with another embodiment of the present invention, there is provided cassette for holding articles to be sterilized. The cassette is comprised of a metallic container that defines a sterilization chamber for holding articles to be sterilized. The container has at least one outer surface. A plurality of spaced-apart, elongated rails extend along the at least one outer surface of the container. Each of the rails have a free, longitudinal edge facing outwardly away from the at least one outer surface of the container wherein the edges of the rails lie in a first plane. An outer insulating shell encases the metallic container and the plurality of rails wherein an outer surface of the insulating shell lies in the first plane.

An advantage of the present invention is a sterilizer for sterilizing medical instruments and medical devices.

Another advantage of the present invention is a sterilizer as described above that utilizes saturated steam at a predetermined temperature.

Another advantage of the present invention is a sterilizer as described above wherein medical instruments and medical devices may be sterilized within a portable cassette.

A still further advantage of the present invention is a sterilizer as described above wherein the cassette is comprised of an inner container defining a sterilizing chamber having an outer shell formed of an insulating material.

A still further advantage of the present invention is a sterilizer as described above wherein the container is comprised of a tray section and a lid section that together defines an inner sterilization chamber.

A still further advantage of the present invention is a sterilizer as described above wherein the tray section and the lid section of the container are formed from metal sheets.

A still further advantage of the present invention is a sterilizer as described above wherein the outer insulating shell includes a lower section and an upper section, the lower section of the shell being dimensioned to receive the tray section of the container and the upper section of the shell being dimensioned to receive the lid section of the container.

A still further advantage of the present invention is a sterilizer as described above wherein the lower section of the insulating shell is dimensioned to be attached to the upper section of the insulating shell with the tray section and the lid section of the container confined therebetween and defining the sterilization chamber.

A still further advantage of the present invention is a sterilizer as described above wherein one of the lid section or the tray section of the container includes a seal element for forming a sealed sterilization chamber.

A still further advantage of the present invention is a sterilizer as described above wherein the sterilization chamber can be pressurized.

A still further advantage of the present invention is a sterilizer as described above wherein the cassette is dimensioned to be inserted into and removed from a receiver unit wherein the cassette is connected to a steam-generating and steam-circulating system.

A still further advantage of the present invention is a sterilizer as described above wherein the receiver unit is operable to engage the outer surface of the cassette when the cassette is positioned therein so as to prevent separation of the shell section during a sterilization cycle.

A still further advantage of the present invention is a sterilizer as described above wherein the cassette is in communication with the steam-generating/steam-circulating system when the cassette is positioned within the receiver unit.

A still further advantage of the present invention is a sterilizer as described above wherein the receiver unit constrains separation of the sections of the cassette when pressure is introduced into the sterilization chamber.

A still further advantage of the present invention is a sterilizer as described above wherein the metal container is formed from thin metal sheets to reduce heat transfer to the cassette.

A still further advantage of the present invention is a sterilizer as described above wherein the cassette includes an inlet port for introducing steam into the sterilization chamber and an outlet port for exhausting steam and condensate from the sterilization chamber.

A still further advantage of the present invention is a sterilizer as described above wherein the cassette closely fits within the receiver chamber to enable the receiver to provide structural support to keep the cassette from separating when pressure is introduced into the sterilization chamber.

A still further advantage of the present invention is a sterilizer as described above wherein the receiver unit includes a plurality of spaced-apart, frame-like elements surrounding the receiver chamber.

A still further advantage of the present invention is a sterilizer as described above wherein the frame-like elements surrounding the receiver chamber provide structural support to withstand pressure loading of the cassette.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 7 is an exploded view, showing a lid section and a tray section of a metal container and a seal assembly that form part of a cassette.

DETAILED DESCRIPTION OF PREFERRED EMBODIMENT

Figure 1:
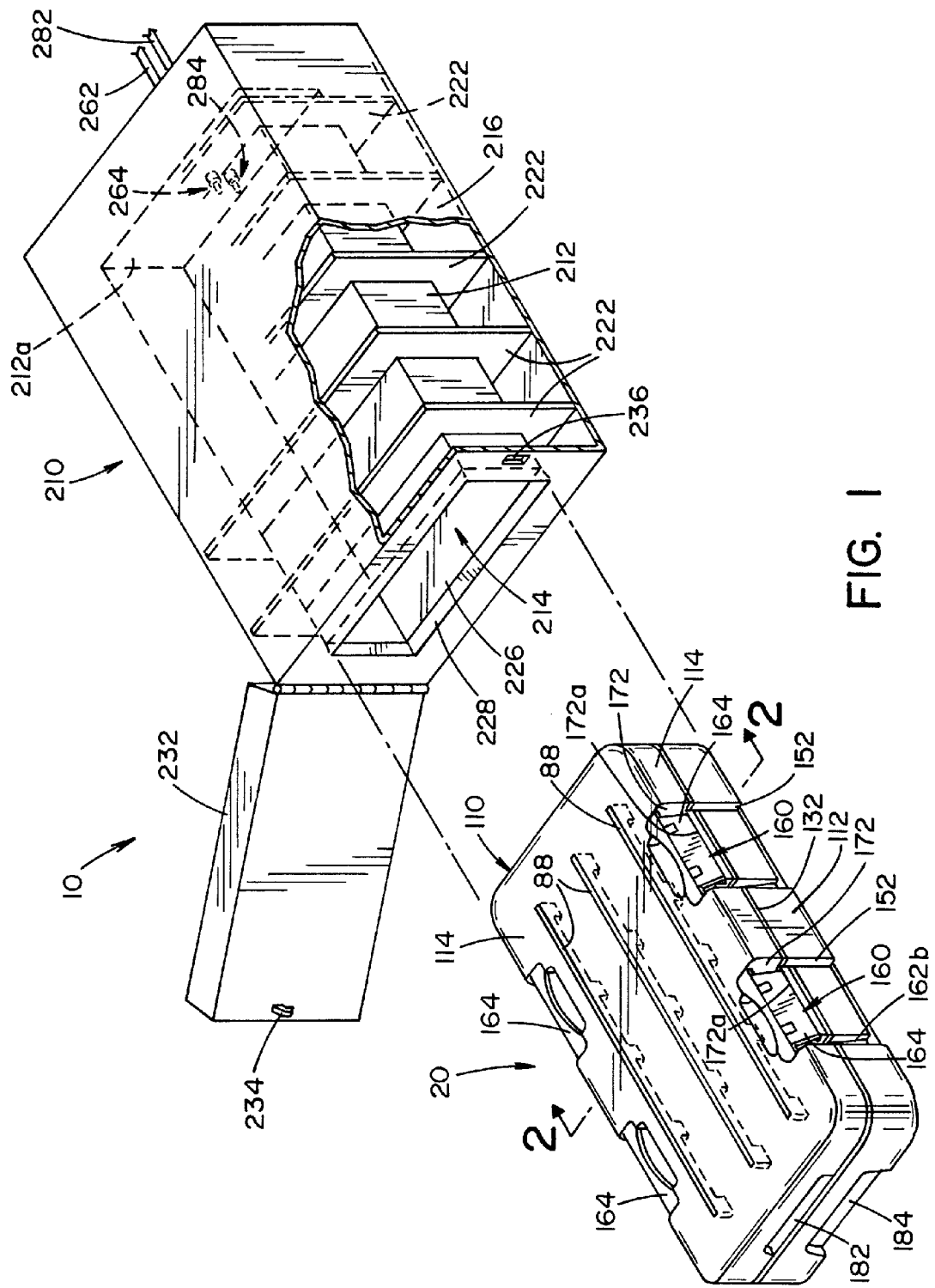
FIG. 1 is an exploded perspective view of a cassette and a receiver unit from a sterilizer according to the present invention.

Referring now to the drawings wherein the showing is for the purpose of illustrating a preferred embodiment of the invention only and not for the purpose of limiting same, FIG. 1 shows a cassette 20 and receiver unit 210 that form part of a sterilizer 10, illustrating a preferred embodiment of the present invention. Cassette 20 is comprised of an inner, rigid container 30 encased within a shell 110 of an insulating material.

Container 30, best seen in FIG. 7, is comprised of a tray section 32 and a lid section 72. Tray section 32 is generally rectangular in shape and has a flat, planar bottom wall 32a, spaced-apart planar, parallel side walls 32b, 32c, a front wall 32d and a back wall 32e. Bottom wall 32a, side walls 32b, 32c, front wall 32d and back wall 32e define a generally rectangular structure having an opened upper end. A flange 32f extends outwardly from the upper edges of side walls 32b, 32c and front and back walls 32d, 32e and defines an upward-facing, planar tray flange surface 36. Tray section 32 is preferably formed of a metal and, more preferably, from a non-corrosive metal. In a preferred embodiment of the present invention, tray section 32 is formed of stainless steel, and tray section 32 is formed by a deep drawing process from a single, flat sheet of stainless steel. The deep drawing process produces rounded, contoured corners and edges at the locations where bottom wall 32a, side walls 32b, 32c, front wall 32d, back wall 32e and flange 32f meet.

Figure 5:
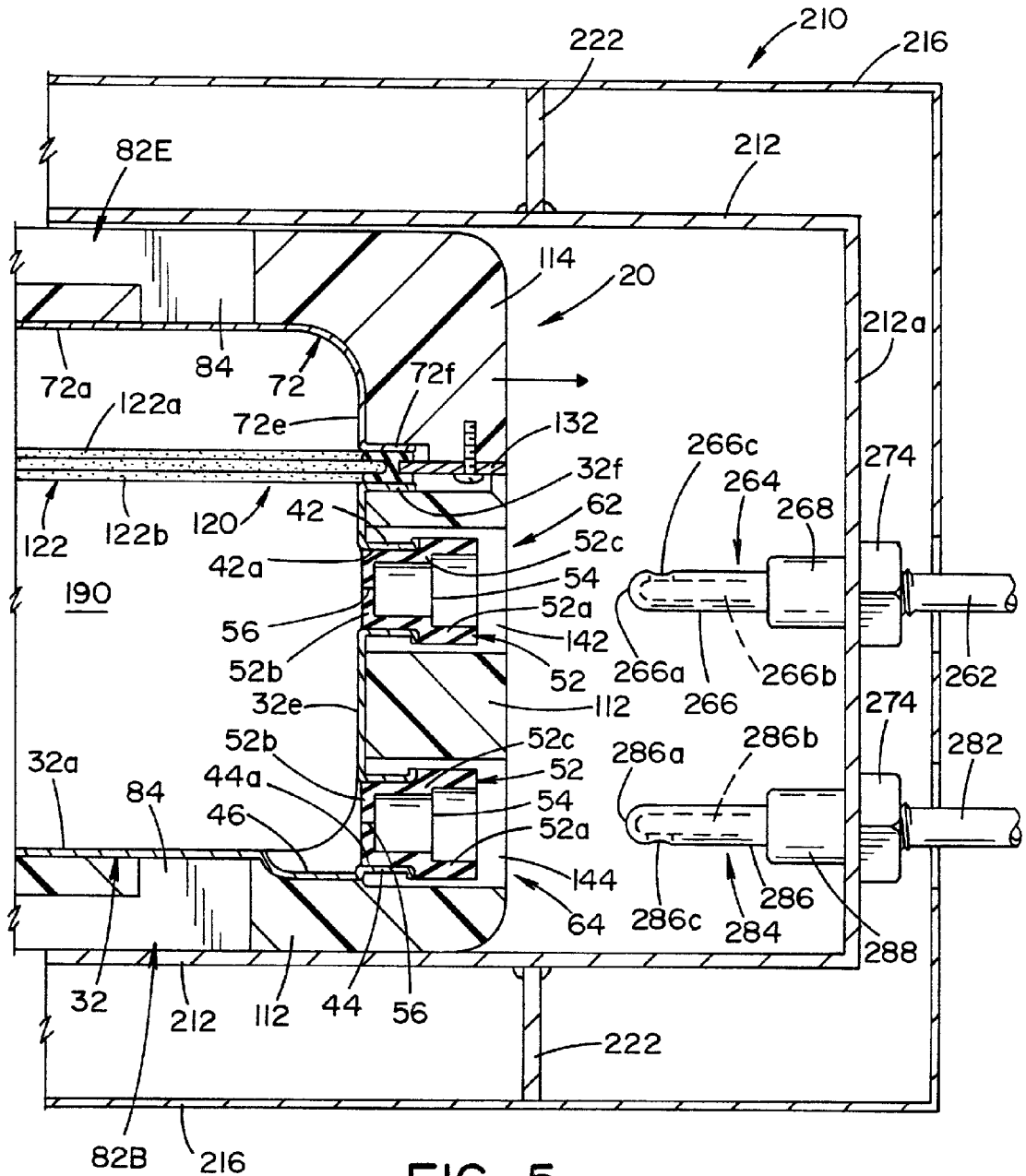
FIG. 5 is an enlarged, side elevational, sectional view, showing the back end of the receiver unit as the cassette is being inserted into the receiver chamber, and further showing connectors on the receiver connecting ports on the end of the cassette to the steam-generating and steam-circulating system.
Figure 6:
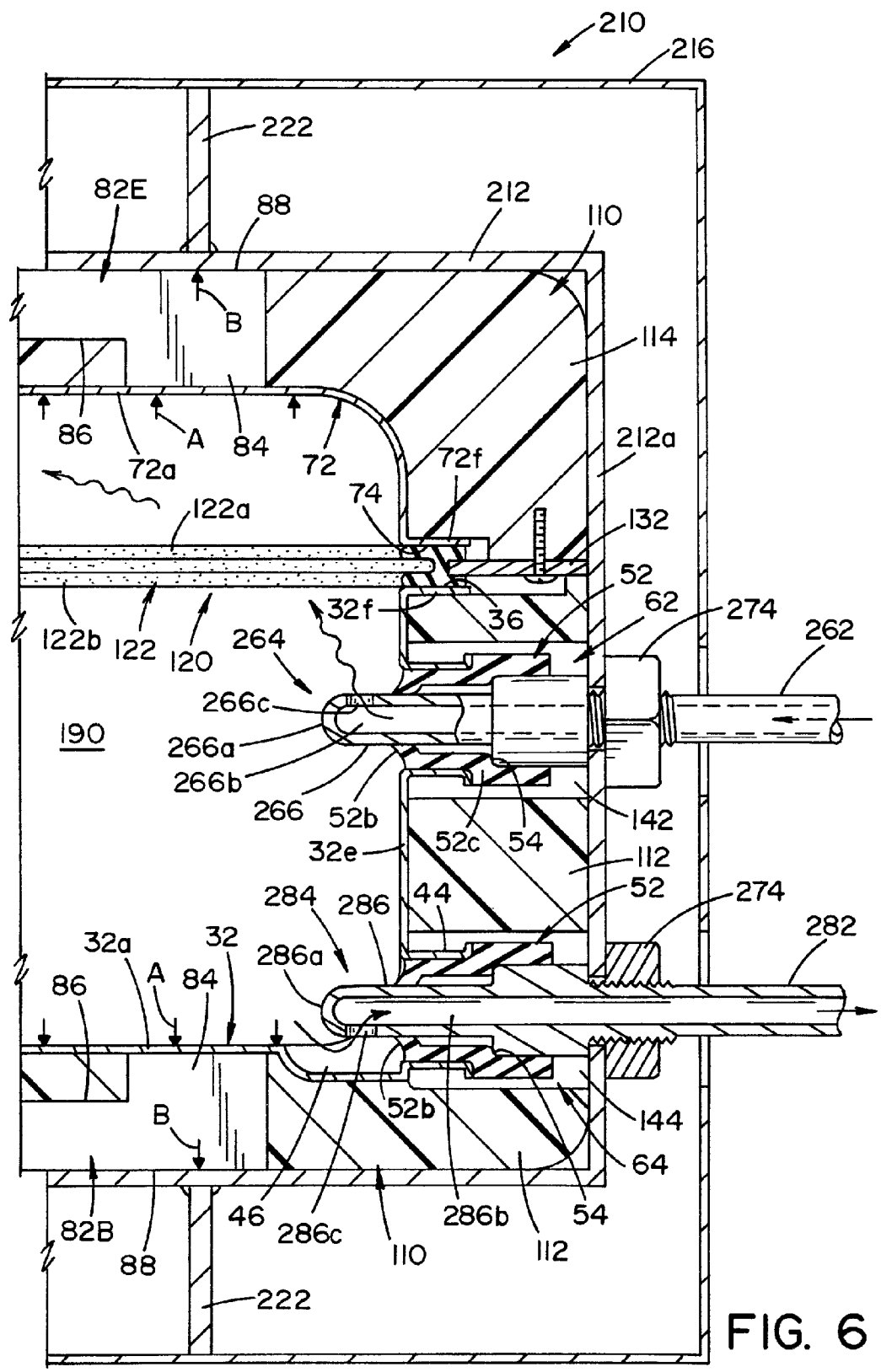
FIG. 6 is an enlarged, side elevational, sectional view similar to FIG. 5, showing the cassette fully inserted into the receiver chamber and showing connectors on the receiver seated within ports in the cassette.

Two spaced-apart, cylindrical sleeves 42, 44 are attached to the outer surface of back wall 32e of tray section 32, as best seen in FIG. 5. Sleeves 42, 44 define openings 42a, 44a that extend from the exterior of tray section 32 into the space defined by tray section 32. Sleeve 44 is disposed on the back wall such that opening 44a therethrough is generally aligned with the surface of bottom wall 32a. A well or recess 46, best seen in FIGS. 5 and 6, is formed in bottom wall 32a of tray section 32 where opening 44a communicates with bottom wall 32a. Sleeve 42 is disposed on back end wall 32e such that opening 42a is near the upper edge of back end wall 32e. In other words, opening 42a is disposed above opening 44a in relation to bottom wall 32a. Sleeves 42, 44 are preferably formed of stainless steel and are attached to tray section 32 by welding or brazing.

Each sleeve 42, 44 is dimensioned to receive a cylindrical cup-shaped member 52 formed of a resilient, flexible material, such as by way of example, butyl rubber or silicone rubber. Cup-shaped members 52 have a cylindrical side wall 52a and a generally planar bottom wall 52b. Cylindrical side wall 52a is formed to include a stepped portion 52c that defines an annular surface 54, best seen in FIG. 5.

Figure 2:
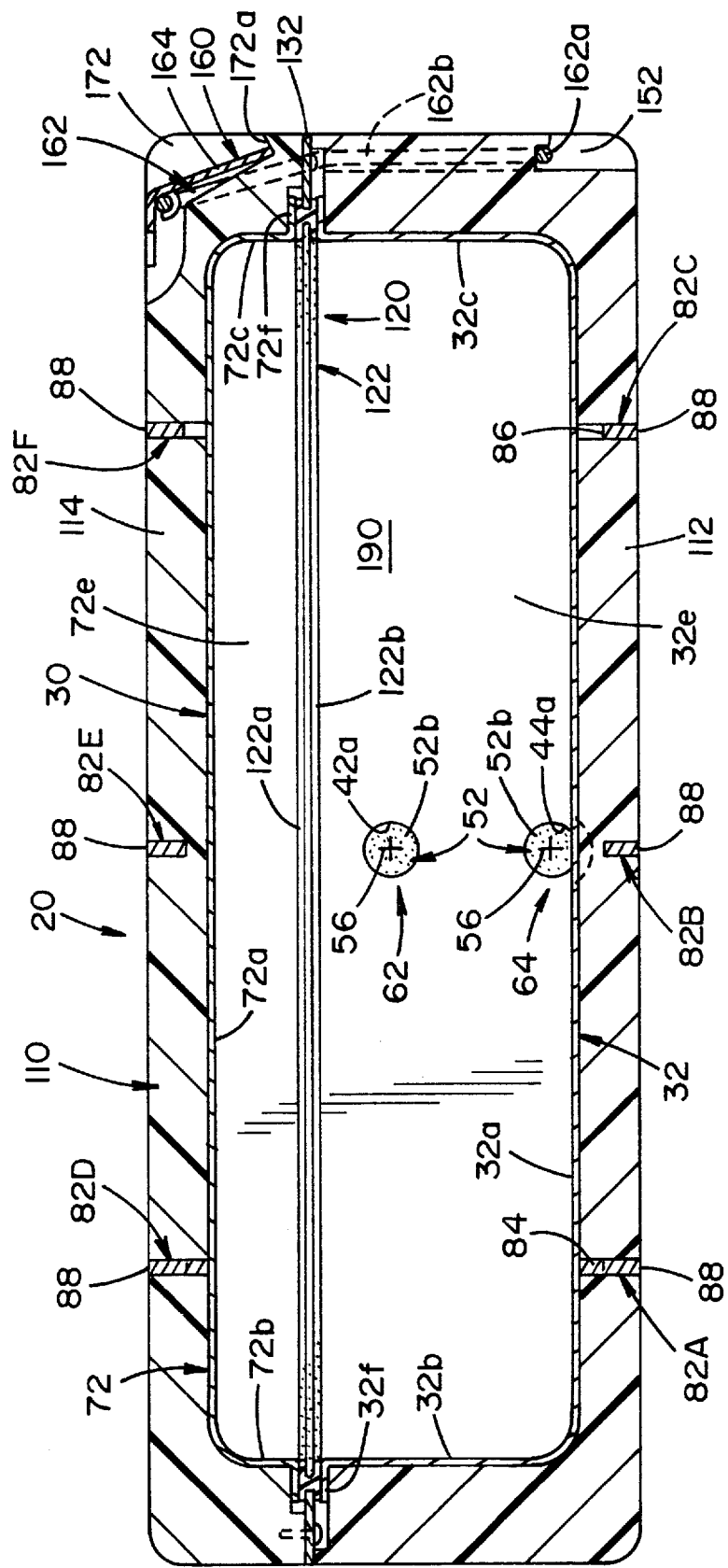
FIG. 2 is an enlarged sectional view of the cassette taken along lines 2-2 of FIG. 1.

Bottom wall 52b of each cup-shaped member 52 includes a slit or incision 56 therein, as best seen in FIG. 2. Cup-shaped member 52 acts as a flow check valve. As shall be described in greater detail below, sleeve 42 and cup-shaped member 52 therein define an inlet port 62. Sleeve 44 and cup-shaped member 52 therein define an outlet port 64.

Lid section 72 is dimensioned to mate with tray section 32 of container 30. In this respect, lid section 72 is generally rectangular in shape and includes a flat, planar top wall 72a, two short side walls 72b, 72c, and two short end walls 72d, 72e. A flange 72f is formed along the free edges of side walls 72b, 72c and end walls 72d, 72e. Flange 72f defines a planar, flat flange surface 74 that is dimensioned to mate with flange surface 36 of flange 32f on tray section 32. As best seen in FIGS. 5 and 6, flange 72f on lid section 72 extends outwardly from side walls 72b, 72c and end walls 72d, 72e beyond the edge of flange 32f on tray section 32.

Like tray section 32, lid section 72 is preferably formed of a non-corrosive metal, such as by way of example and not limitation, stainless steel, and is preferably formed by a deep drawing process from a single, flat sheet of stainless steel.

As shown in FIG. 7, tray and lid sections 32, 72 each includes a plurality of spaced-apart, elongated rails or beams 82 that extend lengthwise along the outer surfaces thereof. In the embodiment shown, three rails 82A, 82B, 82C are disposed on the outer surface of bottom wall 32a of tray section 32, and three rails 82D, 82E, 82F are disposed along the outer surface of top wall 72a of lid section 72. Rails 82A-82F are basically identical and each is comprised of elongated metal strip that is designed to be attached to the outer surfaces of tray section 32 or lid section 72. Strips 82A-82F are preferably formed of stainless steel and are attached to tray section 32 and lid section 72 by brazing or welding.

In the embodiment shown, strips 82A-82F are each notched along the edge that is attached to tray section 32 or lid section 72 to define spaced-apart supports or posts 84. Supports or posts 84 define locations for attachment of rails 82A-82F to the outer surfaces of tray section 32 or lid section 72, as best seen in FIG. 7. Elongated openings 86 are defined in the notched areas that are defined between adjacent posts 84 and between a rail 82A-82F and surface of tray section 32 or surface of lid section 72. Each rail 82A-82F includes a free, longitudinal edge 88 that defines a flat surface facing outwardly, away from the outer surface of bottom wall 32a of tray section 32 and away from top wall 72f of lid section 72. The outward-facing surfaces of edges 88 of rails 82A, 82B and 82C lie in a common plane, which plane is preferably parallel to the plane of bottom wall 32a of tray section 32. The outward facing surfaces of edges 88 of rails 82D, 82E and 82F lie in a common plane, which plane is preferably parallel to the plane of top wall 72a of lid section 72.

Shell 110 is formed of an insulating material and encases tray section 32 and lid section 72 that form container 30. In the embodiment shown, shell 110 is comprised of a lower shell section 112 that is dimensioned to cover the outer surface of tray section 32 and an upper shell section 114 dimensioned to cover the outer surface of lid section 72. Upper and lower shell sections 112, 114 of shell 110 may be formed as separate components dimensioned to receive respectively tray and lid sections 32, 72 therein, but, in the embodiment shown, shell sections 112, 114 are each molded respectively onto tray and lid sections 32, 72 of container 30 to be secured thereto. As shown in the drawings, upper and lower sections 112, 114 of shell 110 together form a structure that is generally rectangular in shape and that has parallel side surfaces, parallel end surfaces and parallel top and bottom surfaces.

Shell 110, i.e., upper section 114 and lower section 112, are preferably formed of a tough, polymeric material such as, by way of example and not limitation, a glass-filled nylon, a glass-filled polyester, a polysulfone, a polycarbonate plastic, a thermoplastic polyetherimide (PEI) resin, such as ULTEM® (a registered trademark of Sabic Innovative Plastics IP B.V. Company), or a melt processible rubber (MPR), such as, ALCRYN® (a registered trademark of Ferro Corporation). By being molded onto the tray and lid sections 32, 72 of container 30, the polymeric material fills opening 86 defined by rails 82A-82F and surface of tray section 32 or lid section 72 to help secure the polymeric material onto container 30. Lower section 112 and upper section 114 are preferably dimensioned such that the outer surfaces thereof are flush, i.e., lie in the same plane, as edges 88 of rails 82A-82F. In other words, the edge surfaces of rails 82A-82F are flush with the outer surfaces of lower and upper sections 112, 114.

As best seen in FIG. 7, a seal assembly 120 is provided to be disposed between flange 32f of the tray section 32 and flange 72f of lid section 72. Seal assembly 120 may be comprised of a molded seal element 122 and a retainer plate 132. Seal element 122 is integrally formed of an elastomeric material such as, by way of example and not limitation, rubber, butyl rubber or neoprene. Seal element 122 has a generally H-shaped cross section that defines two spaced-apart leg portions 122a, 122b. Retainer plate 132 is dimensioned to be attached to upper shell section 114 and to capture one end of leg portion 122a of seal element 122 against flange 72f of lid section 72 of container 30, as best seen in FIGS. 5 and 6. As shown in FIGS. 5 and 6, leg portion 122b of seal element 122 is disposed to engage flange surface 36 of flange 32f on tray section 32 and leg portion 122a of seal element 122 is disposed to engage flange surface 74 of flange 72f on lid section 72 of container 30.

Lower section 112 of shell 110 is formed to include two generally cylindrical openings 142, 144 that communicate with back end wall 32e of container 30. Openings 142, 144 are disposed to surround sleeves 42, 44 and cup-shaped members 52, as best seen in FIGS. 5 and 6. In this respect, openings 142, 144 in lower shell section 112 of shell 110 allow access to cup-shaped members 52 on the back end wall 32e of tray section 32.

Two, spaced-apart recesses 152 are formed in each of the side walls of lower shell section 112, as best seen in FIGS. 1 and 2. Spaced-apart recesses 172, best seen in FIG. 2, are also formed in each of the sides of upper shell section 114. Recesses 172 are in alignment with recesses 152 in lower shell section 112. A latching device 160 is dimensioned to be disposed in corresponding recesses 152, 172, as best seen in FIG. 1. Latching device 160 is provided for attaching and securing lid section 32 and upper shell section 114 of cassette 20 to tray section 32 and lower shell section 112 of cassette 20.

Latching device 160 is a conventional over-center, wire bail latch that includes a U-shape bar portion 162 and a latching plate 164. A base portion 162a of U-shape bar portion 162 is rotatably secured in recess 152. Legs 162b of bar portion 162 are bent near a mid portion thereof. Latching plate 164 is rotatably attached to the ends of legs 162b of bar portion 162. As shown in FIG. 2, a first end of latching plate 164 is formed to define a handle portion of latching device 160. A second end of latching plate 164 is dimensioned to be received into a notch 172a defined by recess 172 when latching device 160 secures lid section 32 and upper shell section 114 of cassette 20 to tray section 32 and lower shell section 112 of cassette 20. Latching device 160 secures and attaches the foregoing components in a conventionally known fashion for over-center latches.

As best seen in FIG. 2, latching devices 160 and recesses 172, 152 in upper and lower shell sections 114, 112, respectively, are dimensioned such that latching devices 160 are within the peripheral boundary defined by shell sections 112, 114, when latching devices 160 secure lid section 72 and upper shell section 114 to tray section 32 and lower shell section 112. When attached and latched together, container 30 defines an inner sterilization chamber 190, as best seen in FIG. 2.

Figure 3:
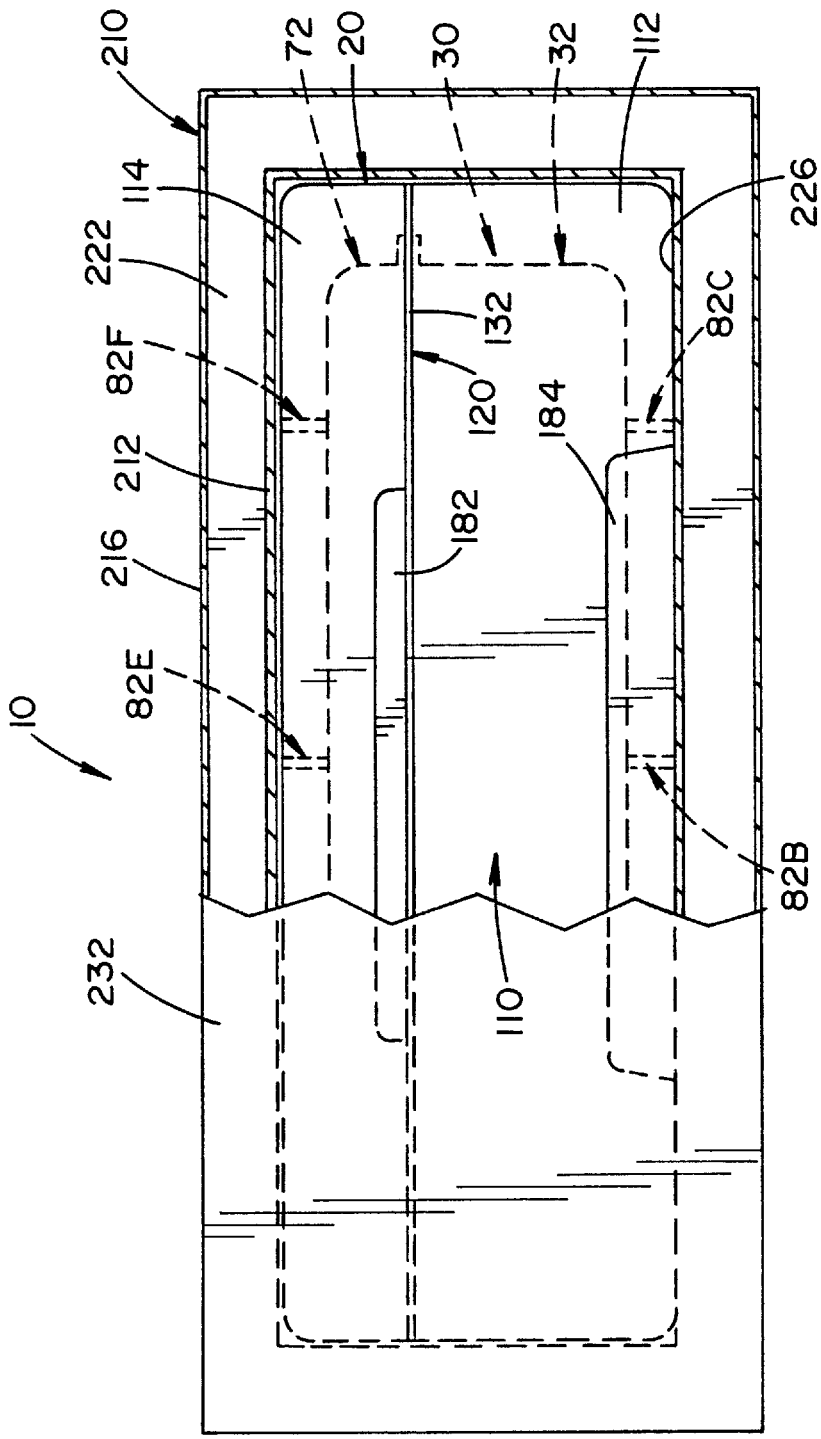
FIG. 3 is a partially sectioned end view of the receiver unit, showing a cassette positioned therein.

As shown in FIGS. 1 and 3, additional recesses 182, 184 are formed in the front end of upper shell section 114 and lower shell section 112, respectively, to define handles for gripping the end of cassette 20.

Figure 4:
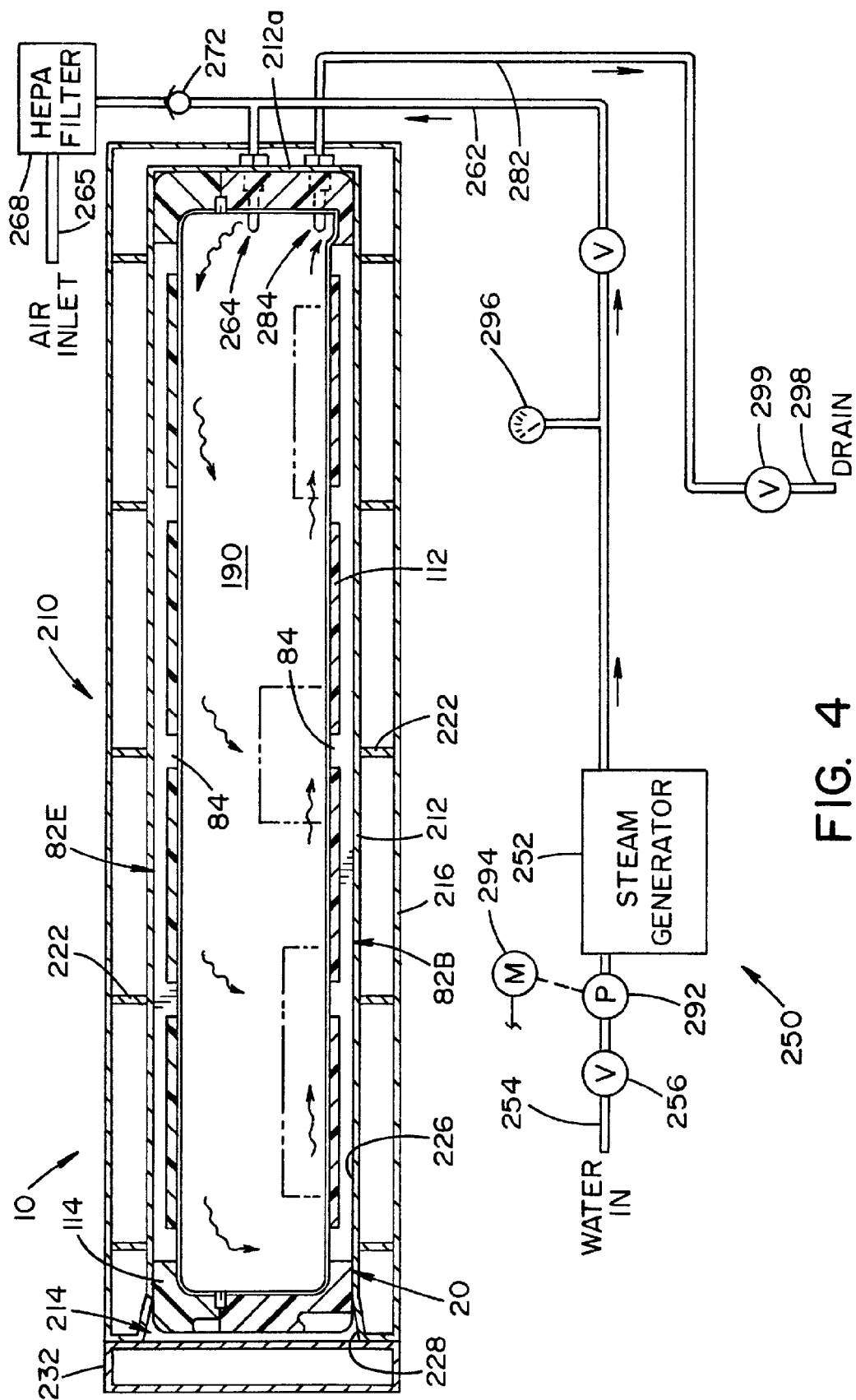
FIG. 4 is a sectional side elevational view of a cassette within the receiver unit, showing the cassette connected to a steam-generating and steam-circulating system that is schematically illustrated and that forms part of the sterilizer according to the present invention.

Referring now to FIG. 1, receiver unit 210 is best seen. Receiver unit 210 is dimensioned to receive cassette 20, and connect cassette 20 to a steam-generating/steam-circulating system 250 (best seen in FIG. 4). Receiver unit 210 is a rectangular structure having an inner rectangular housing 212 defining a rectangular receiver chamber 214. Inner housing 212 is dimensioned such that receiver chamber 214 closely matches the outer dimensions of cassette 20, such that cassette 20 fits snugly within receiver chamber 214. Receiver unit 210 has an outer housing 216 spaced from inner housing 212. Rectangular, frame-shaped ribs 222 are disposed between inner housing 212 and outer housing 216, as illustrated in FIG. 4. Frame-like ribs 222 are preferably formed from a single sheet of flat sheet metal. Ribs 222 are dimensioned to be positioned around inner housing 212 after rectangular inner housing 212 is formed.

An opening 226 is formed in the front end of receiver unit 210 to allow access to receiver chamber 214. The back end of receiver unit 210 is closed by inner and outer housings 212, 216. As best seen in FIG. 4, a leading edge 228 of inner housing 212 is tapered to facilitate insertion of cassette 20 into receiver chamber 214. A double-walled door panel 232 is mounted to receiver unit 210 on a hinge to facilitate opening and closing of opening 226 to receiver chamber 214. A latching element 234 is provided on door panel 232 to attach to a mating latch component 236 on receiver unit 210.

Steam-generating/steam-circulating system 250 best seen in FIG. 4 is connected to the back end of receiving unit 210. Steam-generating/steam-circulating system 250 includes a steam-generator device 252. A water-inlet line 254 is connected to steam generator device 252 to allow water from an external source (not shown) to be introduced into steam generator device 252. A valve 256 controls water flow along water-inlet line 254. A steam-inlet line 262 connects steam generator device 252 to a first male fitting 264 mounted to the back wall 212a of inner housing 212 of receiver unit 210, as best seen in FIGS. 5 and 6. Fitting 264 is comprised of an elongated tubular member 266 having a rounded, closed end 266a and an inner passageway 266b that connects to the passageway defined by steam-inlet line 262. An opening 266c in end 266a connects passageway 266b to the exterior of tubular member 266. Fitting 264 is fixedly mounted to back wall 212a of inner housing 212 by a conventional fastener 274. Fitting 264 includes a positioning collar 268 that is dimensioned to interact with cup-shaped member 52 on cassette 20, as shall be described below. A condensate return line 282 connects a second male fitting 284 to a drain line 298 having a valve 299 therein. Steam-generating/steam-circulating system 250 includes an air inlet line 265. A HEPA filter 268 is disposed within air inlet line 265. A directional check valve 272 is disposed in air inlet line 265 between filter 268 and fitting 264.

In the embodiment shown, second male fitting 284 is basically identical to male fitting 264. Fitting 284 is comprised of an elongated tubular member 286 having a rounded, closed end 286a and an inner passageway 286b that connects to the passageway defined by condensate return line 282. An opening 286c in end 286a connects passageway 286b to the exterior of tubular member 286. Fitting 284 is fixedly mounted to back wall 212a of inner housing 212 by a conventional fastener 274. Fitting 284 includes a positioning collar 288 that is dimensioned to interact with cup-shaped member 52 on cassette 20. Fitting 264 and fitting 284 are disposed on back wall 212a to operatively interact with ports 62, 64 respectively when cassette 20 is fully inserted in receiver chamber 214. In this respect, when cassette 20 is fully inserted into receiver chamber 214, elongated member 266 projects through bottom wall 52b of member 52 in sleeve 42, and elongated member 286 projects through bottom wall 52b of member 52 in sleeve 44, as illustrated in FIG. 6. In this position, passageways 266b and 286b of elongated members 266, 286 communicate with sterilization chamber 190 through opening 266c, 286c, respectively.

Collars 268, 288 on fittings 264, 284 engage annular surfaces 54 and side walls 52a of members 52 in sleeves 42, 44 in sealing fashion, as best seen in FIG. 6.

A pump 292 is disposed in water-inlet line 254. A motor 294 controls operation of pump 292. A pressure gauge 296 is provided in steam-inlet line 262. A controller (not shown) controls operation of valves 256, 299 in water-inlet line 262 and drain line 298, as well as motor 294 that controls pump 292. The controller also monitors the pressure in the steam-inlet line 262. Sensors may also be provided to determine the temperature of the steam generated by steam generator 252.

As illustrated in FIGS. 5 and 6, fittings 264, 284 on steam-inlet line 262 and condensate outlet line 282, respectively, are disposed to be in alignment with cup-shaped members 52 within cassette 20. As illustrated in FIG. 6, when cassette 20 is fully inserted into receiver chamber 214 of receiver unit 210, the outer surface of cassette 20 abuts back wall 212a of inner housing 212 of receiver unit 210. Male fittings 264, 284 project through incisions 56 (see FIG. 2) in bottom wall 52b of resilient cup-shaped members 52, thereby connecting steam inlet line 262 and condensate return line of steam-generating/steam-circulating system 250 with sterilization chamber 190 within cassette 20. Sensors (not shown) may be provided to insure proper seating of cassette 20 within receiver unit 210.

Referring now to the operation of sterilizer 10, sterilization chamber 190 defined by cassette 20 would typically be filled with medical instruments or medical devices (not shown) to be sterilized. The instruments and/or devices would be placed within tray section 32 of cassette 20 and lid section 72 would be placed thereon. The upper cassette section would be attached and latched to the lower cassette section using latching devices 160 provided on the sides of cassette 20. Cassette 20 would then be inserted into receiving chamber 214 of receiving unit 210 until the back wall cassette engages back wall 212a of inner housing 212. In this position, male fittings 264, 284 would project into sterilization chamber 190 within cassette 20, as illustrated in FIG. 6. In this position, passageway in the male fittings 264, 284 communicates with the interior of cassette 20 through openings in male fittings 264, 284.

Steam is then introduced into cassettes 20 by controlling steam generator 252 and pump 292. The introduction of heated steam into sterilization chamber 190 will generally cause an increase in pressure within sterilization chamber 190 as a result of the steam heating the air therein. Air will be forced out of sterilization chamber 190 through opening 286c in male fitting 284. Pressure will build up within sterilization chamber 190 allowing temperatures to rise and sterilization to commence.

In accordance with one aspect of the present invention, the configuration of receiver unit 210 and rails 82A-82F on cassette 20 help receiver unit 210 keep cassette 20 from expanding and the upper cassette sections from separating.

As best seen in FIG. 4, ribs 222 are disposed within receiver unit 210 to be aligned with supports or posts 84 of rails 82A-82F of cassette 20 when cassette 20 is inserted within receiver unit 210.

In this respect, pressure within sterilization chamber 190 exerts an outward force on metal tray section 32 and lid section 72, as illustrated by the arrows "A" in FIG. 6. Any stress exerted on container 30 is transferred through rails 82A-82F embedded within the polymeric material forming insulating shell sections 112, 114 of cassette 20 to the walls of inner housing 212 of receiver unit 210, as illustrated by arrows "B." Because frame-like ribs 222 are integrally formed from a sheet of metal and are welded and secured to inner housing 212 to be aligned with posts 84 of rails 82A-82F, ribs 222 prevent expansion of inner housing 212. Because receiver chamber 214 defined by inner housing 212 closely matches the outer profile of cassette 20, inner housing 212 prevents expansion of cassette 20 and prevents separation of lid section 72 of container 30 from tray section 32 of container 30. Further, the configuration of seal element 122 insures that leg portions 122a, 122b of seal element 122 expand respectively against flange 72f of lid section 72 and flange 32f of tray section 32 because pressure within sterilization chamber 190 tends to separate leg portions 122a, 122b, thereby further insuring that a seal is maintained between lid section 72 of container 30 and tray section 32 of container 30.

After a predetermined period of time, sterilization of the instruments within cassette 20 would be complete. Because of the relatively small mass of metal comprising container 30, heat transferred to cassette 20 during the sterilization cycle is minimized, and the insulating material forming shell 110 around metal container 30 enables cassette 20 to be handled by the user almost immediately following completion of a sterilization cycle. Further, because latching devices 160 are isolated from the container by the insulating material, latching devices 160 may be handled without concern that they may have become overheated during a sterilization cycle. Directional check valve 272 in air inlet line 265 allows clean filtered air to be drawn into sterilization chamber 190 at the completion of a sterilization cycle to prevent a vacuum being formed therein which might prevent cassette 20 from being opened.

Still further, upon removal of cassette 20 from receiver unit 210, the bottom wall 52b of cup-shaped members 52 return to their original normal configuration, as shown in FIG. 5, thus essentially sealing sterilization chamber 190 following a sterilization cycle.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A sterilizer comprised of:
    a receiving unit having a plurality of spaced-apart frame members, each of said frame members having an inner edge defining a generally rectangular opening extending through said frame member, said frame members disposed such that said openings of said frame members define a generally rectangular receiving opening; and
    a generally rectangular cassette dimensioned to be received into said receiving opening of said receiving unit, said cassette comprising:
        a metallic container defining an internal chamber for holding metal instruments or medical devices to be sterilized, said container having an outer surface,
        a generally rectangular insulating shell encasing said container, said insulating shell having an outer surface, and
        a plurality of spaced-apart, elongated rails embedded within said insulating shell, each of said rails extending between said outer surface of said container and said outer surface of said insulating shell, said outer edges defining engaging portions of said cassette that are dimensioned to be disposed adjacent to one or more of said inner edges of said frame members when said cassette is disposed in said receiving unit,
        wherein said plurality of spaced-apart rails of said cassette and said plurality of spaced-apart frame members of said receiving unit limit expansion of said cassette when said internal chamber of said container is pressurized.

2. The sterilizer as defined in claim 1, wherein an inner edge of one or more of said rails engages said outer surface of said container.

3. The sterilizer as defined in claim 1, wherein said outer edge of one or more of said rails is coplanar with said outer surface of said insulating shell.

4. The sterilizer as defined in claim 3, wherein said receiving unit further comprises:
    an inner housing dimensioned to be disposed within said receiving opening, said inner housing having an outer surface dimensioned to engage said inner edges of said frame members and an inner surface dimensioned to engage said outer edges of said rails when said cassette expands.

5. The sterilizer as defined in claim 1, wherein said plurality of spaced-apart frame members of said receiving unit are disposed perpendicular to said plurality of spaced-apart, elongated rails of said cassette.

6. The sterilizer as defined in claim 1, wherein said plurality of spaced-apart frame members are disposed parallel to each other.

7. A sterilizer comprised of:
    a receiving unit having a plurality of spaced-apart frame members, each of said frame members having at least one edge, said frame members disposed such that a plurality of said edges of said frame members define a receiving opening; and
    a cassette dimensioned to be received into said receiving opening, said cassette comprising:
        a container defining an internal chamber for holding metal instruments or medical devices to be sterilized, said container having an outer surface,
        an insulating shell encasing said container, said insulating shell having an outer surface, and
        a plurality of spaced-apart, elongated rails embedded within said insulating shell, each of said rails extending between said outer surface of said container and said outer surface of said insulating shell, one or more of said rails having an outer edge defining an engaging portion of said cassette that is disposed adjacent to one or more of said edges of said frame members of said receiving unit when said cassette is disposed in said receiving opening,
        wherein said plurality of spaced-apart rails of said cassette and said plurality of spaced-apart frame members of said receiving unit limit expansion of said cassette when said internal chamber of said container is pressurized.

8. The sterilizer as defined in claim 7, wherein an inner edge of one or more of said rails engages said outer surface of said container.

9. The sterilizer as defined in claim 7, wherein said outer edge of one or more of said rails is coplanar with said outer surface of said insulating shell.

10. The sterilizer as defined in claim 9, wherein said receiving unit further comprises:
    an inner housing dimensioned to be disposed within said receiving opening, said inner housing having an outer surface dimensioned to engage said edges of said frame members and an inner surface dimensioned to engage said outer edges of said rails when said cassette expands; and
    an outer housing surrounding said inner housing wherein said frame members extend between said inner housing and said outer housing.

11. The sterilizer as defined in claim 7, wherein one or more of said rails of said cassette extend in a first direction along said at least one outer surface of said container and one or more of said frame members of said receiving unit extend in a second direction, said first direction of said rails being perpendicular to said second direction of said frame members.

12. The sterilizer as defined in claim 7, wherein one or more of said rails is notched along said inner edge to define spaced-apart supports or posts.

13. The sterilizer as defined in claim 12, wherein one or more of said frame members align with said spaced-apart supports or posts.

14. The sterilizer as defined in claim 7, wherein said cassette further comprises,
- at least one cylindrical sleeve extending through a side wall of said container, and
- a cup-shaped seal member dimensioned to be received into said at least one cylindrical sleeve.

15. The sterilizer as defined in claim 14, wherein said receiving unit further comprises:
- a fitting dimensioned to engage said seal member, said fitting for fluidly connecting said internal chamber of said cassette to a steam-generating and steam circulating system.

16. The sterilizer as defined in claim 7, wherein said at least one edge of said frame member is an inner edge defining an opening extending through said frame member.

17. The sterilizer as defined in claim 7, wherein said receiving opening is generally rectangular in shape.

18. A sterilizer comprised of:
- a receiving unit having an inner surface, said inner surface defining a receiving opening; and
- a cassette dimensioned to be received into said receiving opening of said receiving unit, said cassette comprising:
  - a container defining an internal chamber for holding metal instruments or medical devices to be sterilized, said container having an outer surface,
  - an insulating shell encasing said container, said shell having an outer surface, and
  - a plurality of spaced-apart, elongated rails embedded within said insulating shell, said rails extending between said outer surface of said container and said outer surface of said insulating shell, one or more of said rails having an outer edge defining an engaging portion of said cassette that is dimensioned to be disposed adjacent to said inner surface of said receiving unit when said cassette is disposed in said receiving opening,
  - wherein said plurality of spaced-apart rails limit expansion of said cassette when said internal chamber of said container is pressurized.

19. The sterilizer as defined in claim 18, wherein an inner edge of one or more of said rails engages said outer surface of said container.

20. The sterilizer as defined in claim 18, wherein said outer edge of one or more of said rails is coplanar with said outer surface of said insulating shell, said outer edge engaging said inner surface of said receiving unit when said container expands.

21. The sterilizer as defined in claim 18, wherein a wall defines said inner surface of said receiving unit, said wall having an outer surface.

22. The sterilizer as defined in claim 21, wherein said receiving unit further comprises:
- a plurality of spaced-apart frame members, each of said frame members having at least one edge engaging said outer surface of said wall of said receiving unit.

23. The sterilizer as defined in claim 22, wherein said at least one edge of said frame member is an inner edge defining an opening extending through said frame member.

24. The sterilizer as defined in claim 22, wherein said plurality of spaced-apart frame members of said receiving unit are disposed perpendicular to said plurality of spaced-apart, elongated rails of said cassette.

25. The sterilizer as defined in claim 22, wherein said plurality of spaced-apart frame members are disposed parallel to each other.

26. The sterilizer as defined in claim 18, wherein said receiving opening is generally rectangular in shape.

27. A cassette for holding articles to be sterilized, said cassette comprised of:
- a container defining an internal chamber for holding said articles to be sterilized, said container having an outer surface;
- an outer insulating shell encasing said container, said insulating shell having an outer surface; and
- a plurality of spaced-apart, elongated rails embedded within said outer insulating shell, said rails extending between said outer surface of said container and said outer surface of said insulating shell.

28. The cassette for holding articles to be sterilized as defined in claim 27, wherein an inner edge of one or more of said rails engages said outer surface of said container.

29. The cassette for holding articles to be sterilized as defined in claim 27, said rails further comprising an inner edge of one or more of said rails, wherein said inner edge of one or more of said rails is notched to define spaced-apart supports or posts and elongated openings between said supports or posts.

30. The cassette for holding articles to be sterilized as defined in claim 29, wherein said outer insulating shell extends into said elongated openings.

31. The cassette for holding articles to be sterilized as defined in claim 27, said rails further comprising an outer edge of one or more said rails, wherein said outer edge of one or more of said rails is coplanar with said outer surface of said insulating shell.

32. The cassette for holding articles to be sterilized as defined in claim 27, wherein said container is comprised of:
- a tray section, and
- a lid section wherein said tray section is attachable to said lid section to define said internal chamber.

33. The cassette for holding articles to be sterilized as defined in claim 32, further comprising:
- a seal assembly disposed between said tray section and the lid section for sealing said internal chamber.

34. The cassette for holding articles to be sterilized as defined in claim 32, further comprising a seal assembly, wherein said seal assembly is comprised of:
- a seal element, and
- a retainer plate for securing said seal element between said tray section and said lid section.

35. The cassette for holding articles to be sterilized as defined in claim 32, further comprising:
- a latching device for securing said tray section to said lid section wherein said outer insulating shell is disposed between said container and said latching device to thermally isolate said latching device from said container.

36. The cassette for holding articles to be sterilized as defined in claim 27, further comprising:
- at least one cylindrical sleeve extending through a side wall of said container, and
- a cup-shaped seal member dimensioned to be received into said at least one cylindrical sleeve.

37. The cassette for holding articles to be sterilized as defined in claim 27, wherein said rails extend in a first direction along said outer surface of said container.

* * * * *